US008618539B2

(12) United States Patent
Henderson et al.

(10) Patent No.: US 8,618,539 B2
(45) Date of Patent: Dec. 31, 2013

(54) INTERCONNECT SENSOR FOR DETECTING DELAMINATION

(75) Inventors: Brian Matthew Henderson, San Diego, CA (US); Shiqun Gu, San Diego, CA (US); Homyar C. Mogul, San Diego, CA (US); Mark M. Nakamoto, San Diego, CA (US); Arvind Chandrasekaran, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 615 days.

(21) Appl. No.: 12/613,444

(22) Filed: Nov. 5, 2009

(65) Prior Publication Data

US 2011/0101347 A1    May 5, 2011

(51) Int. Cl.
*H01L 23/48* (2006.01)
(52) U.S. Cl.
USPC ............ 257/48; 257/508; 257/774; 257/758; 257/E23.011; 257/E23.067; 257/E23.145
(58) Field of Classification Search
USPC ............ 257/48, E21.525, E21.523, E23.179, 257/774, E23.011, E23.067, E23.145, 508, 257/758, E23.174; 438/15, 612, 667; 324/500, 525, 527, 537, 750.3, 750.16, 324/754.01, 763.01
See application file for complete search history.

(56) References Cited

U.S. PATENT DOCUMENTS

| | | |
|---|---|---|
| 2006/0189007 A1 | 8/2006 | Aoki et al. |
| 2006/0290002 A1 | 12/2006 | Arana et al. |
| 2008/0246491 A1 | 10/2008 | Ogawa et al. |
| 2009/0015285 A1 | 1/2009 | Farooq et al. |
| 2009/0246892 A1 | 10/2009 | Maloney et al. |
| 2011/0031581 A1* | 2/2011 | West .............................. 257/508 |

OTHER PUBLICATIONS

International Search Report and Written Opinion—PCT/US2010/055426—International Search Authority, European Patent Office,Jan. 26, 2011.
Written Opinion—PCT/ US2010/055426, International Search Authority—European Patent Office Jan. 26, 2011.

* cited by examiner

*Primary Examiner* — Ha Tran T Nguyen
*Assistant Examiner* — Suberr Chi
(74) *Attorney, Agent, or Firm* — Michelle S. Gallardo (57) ABSTRACT

An interconnect sensor for detecting delamination due to coefficient of thermal expansion mismatch and/or mechanical stress. The sensor comprises a conductive path that includes a via disposed between two back end of line metal layers separated by a dielectric. The via is coupled between a first probe structure and a second probe structure and mechanically coupled to a stress inducing structure. The via is configured to alter the conductive path in response to mechanical stress caused by the stress inducing structure. The stress inducing structure can be a through silicon via or a solder ball. The dielectric material can be a low-k dielectric material. In another embodiment, a method of forming an interconnect sensor is provided for detecting delamination.

18 Claims, 6 Drawing Sheets

INTERCONNECT SENSOR FOR DETECTING DELAMINATION

FIELD OF DISCLOSURE

This disclosure relates generally to a sensor for an integrated circuit package, and in particular to an interconnect sensor for detecting delamination due to materials having different coefficients of thermal expansion.

BACKGROUND

In electronic packaging, chips can be stacked in a three-dimensional configuration. A through silicon via ("TSV") can be used for coupling two chips in the package. The TSV is formed of a conductive material that passes through the silicon wafer to electrically couple the chips. The conductive material, such as copper, has a different coefficient of thermal expansion ("CTE") than the surrounding silicon. For example, the CTE of copper is approximately five times greater than the CTE of silicon. During a temperature cycle, the conductive material in the TSV can expand and contract. In effect, the conductive material can impose a force on the dielectric material that surrounds the TSV.

Over the course of one or more temperature cycles, the dielectric material can weaken and begin to crack. Connections between conductive materials can break causing open circuits to develop, or conductive materials separated by dielectric material can be damaged resulting in leakage. This breaking or cracking is particularly problematic with low-k dielectric materials. Low-k dielectric materials are often used for minimizing capacitance between the metal layers. However, low-k dielectric materials have weak mechanical strengths and are subject to breaking near the interface of the conductive material and the low-k dielectric material. As a result, there are reliability concerns with three-dimensional chip stacking in an electronic package. It also has been found that cracking is not always predictable and depends on the properties of the materials, feature sizes, and geometries used plus external factors such as mechanical stresses and temperature cycling. Therefore, it would be desirable to develop a sensor and method of use for detecting damage to the low-k dielectrics over the course of repeated thermal cycles before delamination occurs.

SUMMARY

For a more complete understanding of the present disclosure, reference is now made to the following detailed description and the accompanying drawings. In an exemplary embodiment, a sensor for detecting delamination is provided. The sensor comprises a first probe structure and a second probe structure. The sensor also includes a via disposed between at least two back end of line metal layers which are separated by a dielectric. The via forms a conductive path between the first probe structure and the second probe structure. The via is also mechanically coupled to a stress inducing structure such that the via is configured to alter the conductive path in response to mechanical stress caused by the stress inducing structure. The stress inducing structure can be a through silicon via or a solder ball.

In another embodiment, an interconnect sensor is provided for detecting delamination. The sensor comprises a first conductive path and a second conductive path. The first and second conductive paths are at least partially parallel and mechanically coupled to a stress inducing structure. The conductivity between the first and second conductive paths may be altered in response to stress caused by the stress inducing structure. The stress inducing structure can be a through silicon via or a solder ball.

In one form of this embodiment, the first and second conductive paths can form comb structures. A serpentine conductive path can be disposed between the first and second conductive paths. In another form of this embodiment, the first and second conductive layers can be fabricated in the same or different back end of line metal layers.

In a different embodiment, a method of forming an interconnect sensor is provided for detecting delamination. The method comprises forming a conductive path between at least two back end of line metal layers. The at least two back end of line metal layers are separated by a dielectric material such as a low k dielectric. The conductive path can be coupled between a first probe structure and a second probe structure and mechanically coupled to a stress inducing structure. A via can be fabricated between the at least two back end of line metal layers. The sensor can be adapted to detect delamination by measuring signal continuity or resistance.

In another exemplary embodiment, a method of forming an interconnect sensor is provided for detecting delamination. The method comprises fabricating a first conductive path and a second conductive path at least partially parallel to one another. The first and second conductive paths are separated by a dielectric layer. The first and second conductive paths are coupled to a stress inducing structure. The first and second conductive paths can be fabricated as comb structures and a serpentine conductive path can be fabricated therebetween. The sensor can be adapted to detect delamination by measuring signal continuity, capacitance, or resistance.

DETAILED DESCRIPTION

Figure 1:
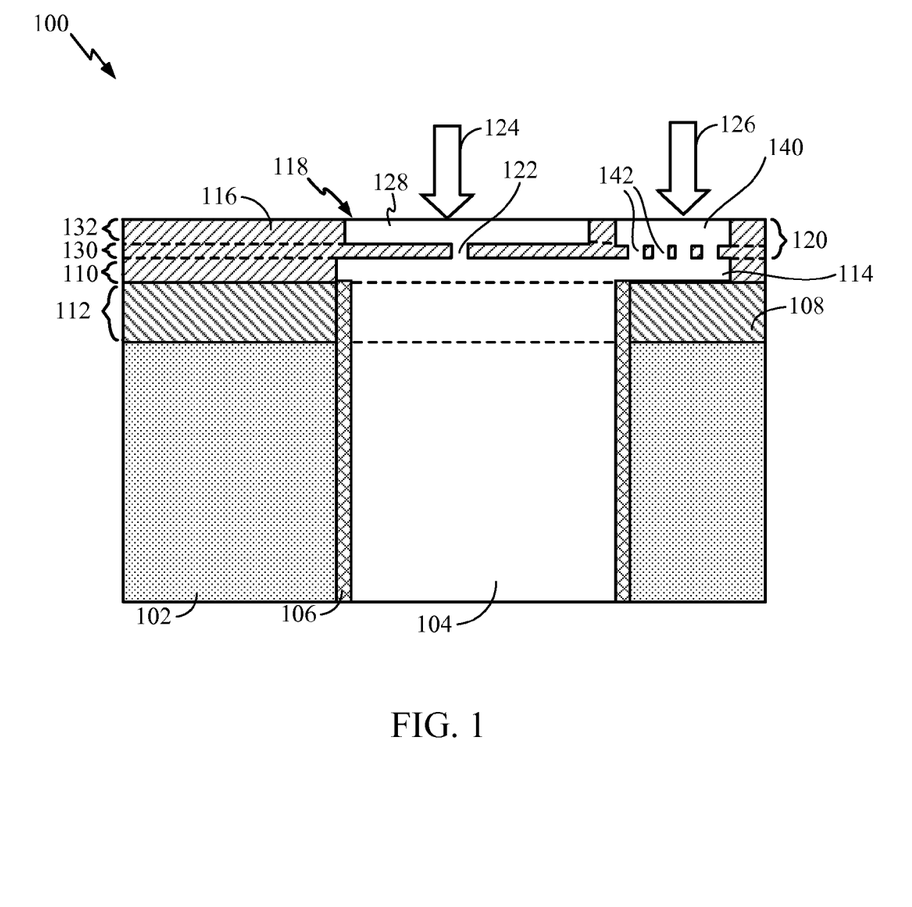
FIG. 1 is a schematic view of an exemplary embodiment of an interconnect sensor for detecting delamination in an electrical package.

Referring to the exemplary embodiment shown in FIG. 1, an electrical package is shown. The package includes an interconnect sensor 100 for detecting delamination of a dielectric material between back end of line (BEOL) layers. A substrate 102 made of silicon or other known substrate material is provided with a through silicon via (TSV) 104 disposed therein. The TSV 104 is fabricated from conductive material such as copper or other known conductive material. A TSV liner or oxide layer 106 such as silicon dioxide ($SiO_2$) surrounds the conductive material of the TSV 104 and can separate the conductive material from the substrate 102.

As described above, the interconnect sensor 100 is provided in the BEOL portion of the integrated circuit. As such, active components can be integrated into the package. A contact layer 112 that couples a first metal layer 110 to the substrate 102 can be provided. Disposed between the first metal layer 110 and the substrate 102 is an oxide layer 108. The oxide layer 108 can be silicon dioxide, for example.

The BEOL also can include additional metal layers, although in FIG. 1 only the first metal layer 110 and second metal layer 132 are shown. A dielectric material or layer 116, such as a low-k dielectric, can be used in the BEOL. The low-k dielectric can be silicon dioxide, for example, or any other known dielectric material having a small dielectric constant. The low-k dielectric provides insulation between conductive layers and active components, and in particular, can reduce parasitic capacitance. As components such as transistors are placed in closer proximity to one another as feature sizes decrease, the low-k dielectric advantageously reduces the capacitance and cross-talk between components.

However, as described above, low-k dielectric materials may be weak during thermal cycling and are subject to delamination. For example, stress-inducing structures such as the TSV 104 in FIG. 1 can impose stress on the low-k dielectric material 116, and causes the dielectric to begin breaking apart. The low-k dielectric can break apart because it is a porous material, and cracking in the dielectric can adversely affect the insulation between metal layers in the interconnect. In the case of the TSV 104, thermal cycling can cause the conductive material of the TSV 104 to expand as the temperature therein increases and contracts as temperature decreases. As the conductive material expands, the TSV 104 can push or move against the dielectric 116. However, once the TSV 104 begins to contract, the dielectric material 116 can crack or break apart at or near the TSV 104. Besides the possible loss of insulation between metal layers, there is an overall reliability concern associated with the package.

During thermal cycling, it has been found that low-k dielectric materials do not undergo delamination in a systematic manner. As such, the test structure including the sensor 100 can be placed in several locations along the die. Testing could then be implemented to determine what factors, such as temperature, stress, number of cycles, etc., have the most impact on yield. Design guidelines could then be established from the results. Other advantages and uses of the interconnect sensor 100 can be implemented as understood by one skilled in the art.

In the embodiment of FIG. 1, for example, a via 122 is fabricated in a via layer 130, which is disposed between the first metal layer 110 and the second metal layer 132. The via 122 is part of an electrically conductive path that includes a first sensor segment 114 and a second sensor segment 128. The first sensor segment 114 comprises conductive material such as copper and is disposed in the first metal layer 110. Likewise, the second sensor segment 128 is formed of conductive material such as copper and is disposed in the second metal layer 132.

The diameter or width of the via 122 can be significantly smaller than the width of the first metal layer 110 and second metal layer 132. As described above, the TSV 104 will induce mechanical stress on the via 122 as the TSV 104 expands and contracts during thermal cycling. The dielectric material 116 surrounding the via 122 is therefore subject to cracking or delaminating during the thermal cycling.

To detect cracking or delaminating of the dielectric material 116, a conductive path is established in the BEOL by fabricating a first probe structure 118 and a second probe structure 120. The second probe structure 120 comprises a probe pad 140 and an array of vias 142 which couple the probe pad 140 to the first sensor segment 114. In this embodiment, the second sensor segment 128 serves as a probe pad for the first probe structure 118. However, in other embodiments, a separate probe pad may be fabricated for the first probe structure 118. The first and second probe structures 118, 120 are adapted to be coupled to terminals or pads 124, 126, respectively, of a probe device. The architectural design of the first and second probe structures is described in further detail with respect to FIG. 2.

An electrical signal can be applied to test continuity of the sensor 100 through the first probe structure 118, the second sensor segment 128, the via 122, the first sensor segment 114 and the second probe structure 120. If the sensor 100 exhibits a lack of continuity or increased resistance in the signal, for example, the dielectric material 116 may have cracked or failed. As such, the sensor 100 provides for the detection of delamination in the dielectric material 116.

Figure 2:
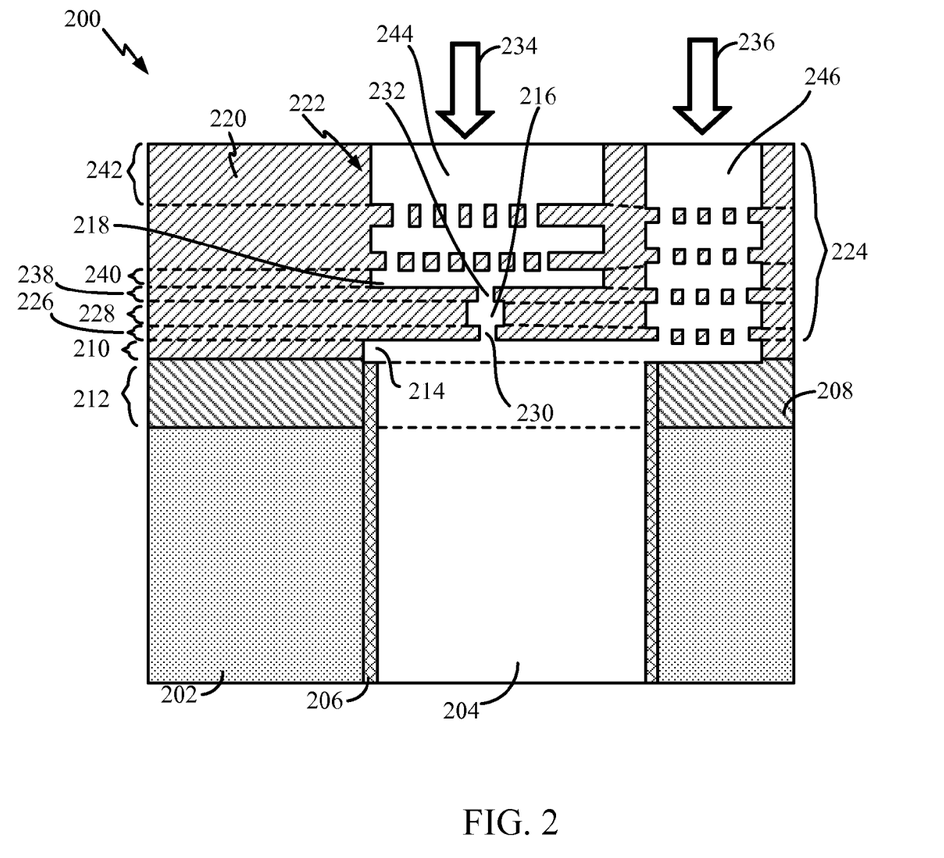
FIG. 2 is a schematic view of another embodiment of an interconnect sensor for detecting delamination in an electrical package.

With reference to FIG. 2, another embodiment of an interconnect sensor is provided for detecting delamination of a dielectric material. In this embodiment, a TSV 204 is fabricated in a silicon substrate 202 with an oxide layer 206 disposed therebetween. Again, an active component can be placed in the BEOL along with a contact layer 212 that couples a first metal layer 210 (i.e., Metal 1) to the substrate 202. The first metal layer 210 is also electrically coupled to the conductive material of the TSV 204. An oxide layer 208 such as silicon dioxide is provided between the first metal layer 210 and substrate 202.

A dielectric material 220 such as a low-k dielectric insulates various metal layers in the BEOL. In FIG. 2, for example, a first sensor segment 214 is disposed in the first metal layer 210 and a second sensor segment 216 is disposed in a second metal layer 228. The first sensor segment 214 is coupled to the second sensor segment 216 by a first via 230, which is fabricated in a first via layer 226. The first sensor segment 214, first via 230, and second sensor segment 216 are formed of conductive material such as copper, for example. A third sensor segment 218 is fabricated in a third metal layer 240. The third sensor segment 218 is coupled to the second sensor segment 216 by a second via 232, which is fabricated in a second via layer 238. The second via 232 and third sensor segment 218 are formed of conductive material such as copper.

Additional metal layers can be included in the BEOL and a plurality of vias can couple the additional metal layers to form a continuous conductive path. Similar to the embodiment of FIG. 1, a first probe structure 222 and a second probe structure 224 are provided in the embodiment of FIG. 2. The first probe structure 222, also referred to as a first probe terminal, can include a contact or pad 244 at one end thereof to which a first sensor probe 234 can couple and a plurality of metal structures and vias which couple the first probe structure 222 to the third sensor segment 218. The second probe structure 224, also referred to as a second probe terminal, can also include a contact or pad 246 at one end thereof to which a second sensor probe 236 can couple and a plurality of metal structures and vias which couple the second probe structure 224 to the first sensor segment 214. The contacts or pads 244, 246 are both formed in the uppermost metal layer 242.

The first and second probe structures 222, 224, respectively, can be fabricated from various metal conductive layers. Each structure can have a generic design, i.e., there does not need to be any special architecture associated with either structure. Instead, both structures need to provide sufficient terminal connections for the sensor so that an electrical signal can be passed from the first sensor probe 234 to the second sensor probe 236. Each probe structure can include a plurality of metal layers, each of which is coupled by one or more vias to form an electrically conductive structure.

As the TSV 204 undergoes thermal cycling, the conductive TSV 204 expands and contracts. This induces mechanical stress on the first via 230 and second via 232, thereby potentially causing the dielectric material 220 to break or crack at or near the vias 230, 232. The breaking or cracking of the dielectric material 220, i.e., delamination, can be detected by forming a circuit through the sensor 200. The first sensor probe 234 is coupled to the pad 244 of the first probe structure 222 and the second sensor probe 236 is coupled to the pad 246 of the second probe structure 224. An electrical signal can be passed from the first sensor probe 234 to the second sensor probe 236 through the sensor 200 to detect discontinuity in the signal or a change in a resistance of the sensor 200, for example.

Figure 3:
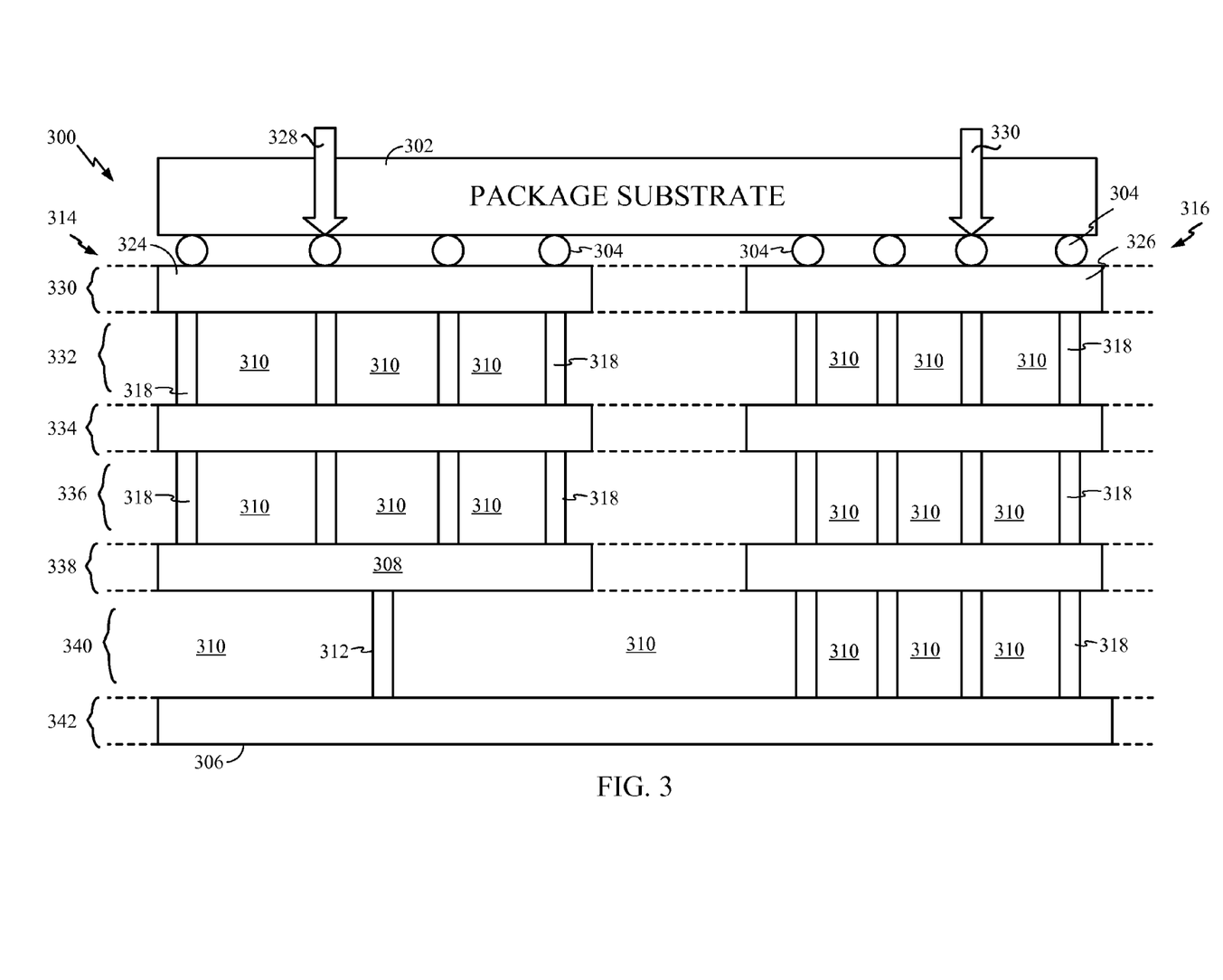
FIG. 3 is a schematic view of a different embodiment of an interconnect sensor for detecting delamination in an electrical package.

A different embodiment of a sensor 300 for detecting delamination of a dielectric material 310 is shown in FIG. 3. In FIG. 3, a plurality of solder balls 304 are shown coupled to a package substrate 302. The plurality of solder balls 304 comprise a stress-inducing structure similar to the TSV of FIGS. 1 and 2. During thermal cycling, each solder ball 304 can transmit mechanical stress to dielectric material 310 disposed between multiple metal layers. In the embodiment of FIG. 3, stress imposed by the plurality of solder balls 304 can be transmitted to a via 312 coupled between a first sensor segment 306 and a second sensor segment 308. The first sensor segment 306 is fabricated in a first metal layer 342 and the second sensor segment 308 is fabricated in a second metal layer 338. The via 312 is fabricated in a first via layer 340. As the plurality of solder balls 304 impose stress to the via 312 during thermal cycling, the dielectric material 310 that surrounds the via 312 is subject to breaking or cracking.

To enhance the reliability of the package, the interconnect sensor 300 includes a first probe structure 314 and a second probe structure 316. The first probe structure 314 and second probe structure 316 can include a plurality of metal layers and vias. In FIG. 3, for example, the first and second probe structures can comprise sensor segments in a third metal layer 334 and fourth metal layer 330. In other embodiments, additional or few metal layers can form the probe structures. Each sensor segment can be coupled by vias 318, which can be fabricated in a second via layer 336, a third via layer 332, and so forth. The vias 318 are substantially parallel and vertically aligned with one another. The first probe structure 314 includes a first terminal or pad 324 that is formed in the uppermost metal layer (e.g., fourth metal layer 330 of FIG. 3). Likewise, the second probe structure 316 includes a second pad or terminal 326 that is formed in the uppermost metal layer.

Sensor probes 328, 330 can electrically couple to the pads 324, 326 and pass an electrical signal through a circuit or conductive path created between the two probe structures and detect signal discontinuity or a change in resistance. To do so, an electrical circuit or path can be fabricated in the substrate 302 to allow a signal to pass through the substrate 302 to one or more of the solder balls 304. One or more pads can also be provided in the substrate 302 to allow the sensor probes 328, 330 to come into contact therewith and pass the signal through the electrical circuit or path in the substrate 302. In effect, the electrical circuit or path in the substrate 302 provides the sensor probes 328, 330 with access to the pads 324, 236. The signal then passes from the first terminal 324 to the second terminal 326 through the multiple metal layers and vias of the first and second probe structures 314, 316, the first and second sensor segments 306, 308, and the via 312. As the plurality of solder balls 304 imposes stress to the via 312, any breaking or cracking of the dielectric material 310 that surrounds the via 312 can be detected by the sensor 300.

Figure 4:
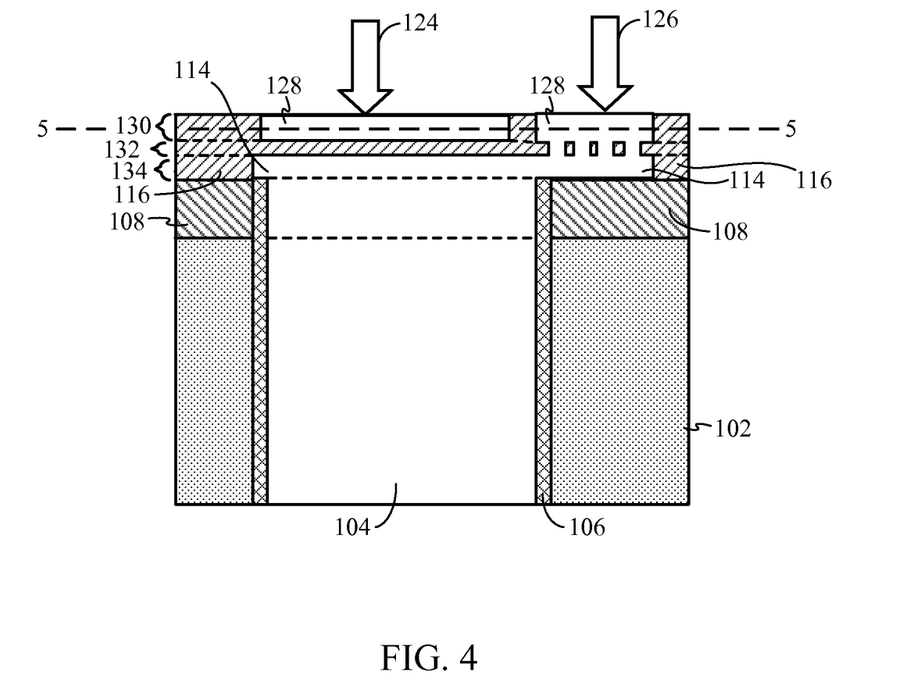
FIG. 4 is a schematic view of an embodiment of an interconnect sensor for detecting delamination in a single metal layer in an electrical package.
Figure 5:
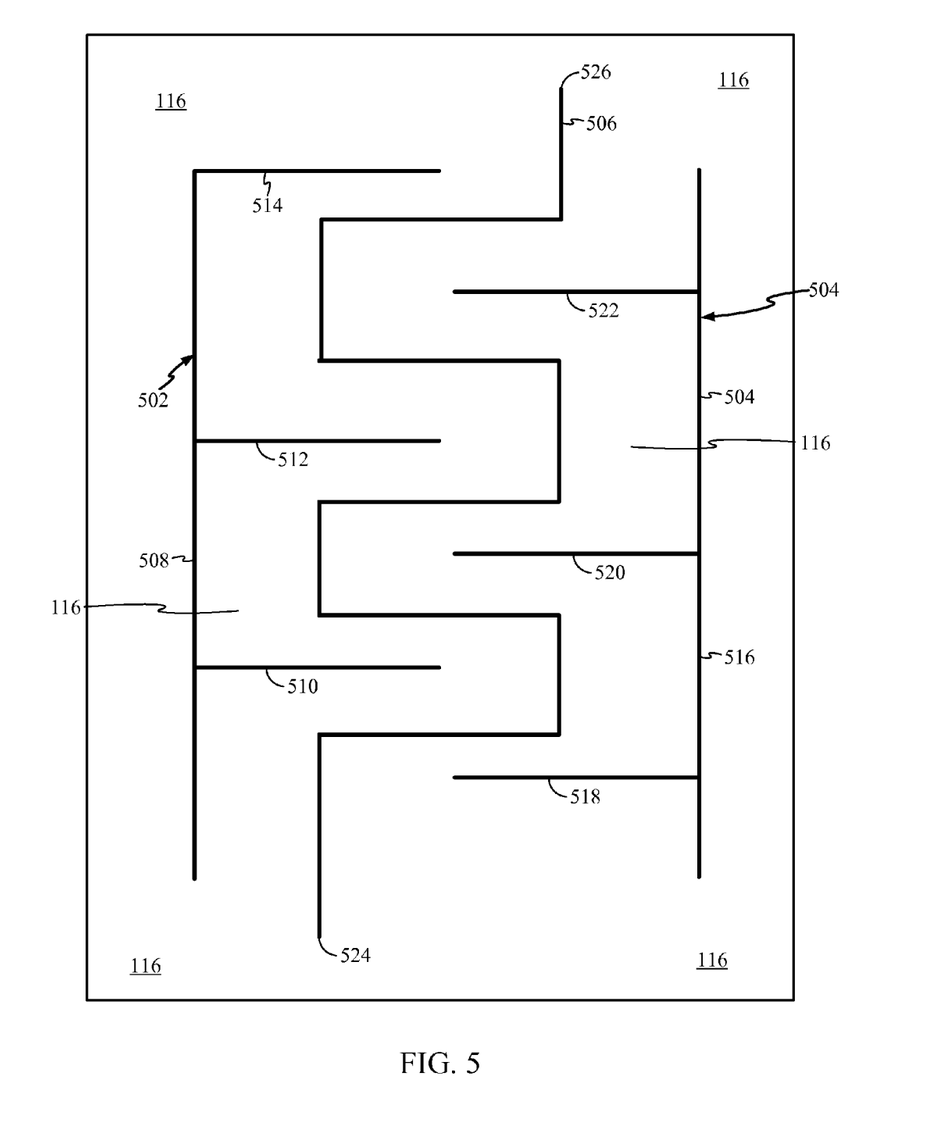
FIG. 5 is a cross-sectional and schematic view taken along line 5-5 of FIG. 4 of a single metal layer with a conductive path for detecting delamination therein.

With reference to FIGS. 4 and 5, another exemplary embodiment of an interconnect sensor for detecting delamination of a dielectric material is provided. The embodiment of FIG. 4 is similar to FIG. 1 with reference numbers indicating the same structural features; however, there is no via coupling the first sensor segment 114 and second sensor segment 128. As such, there is no electrical circuit formed between the first probe 124 and second probe 126.

In FIG. 5, a first comb structure 502 and a second comb structure 504 are fabricated conductive paths in the second sensor segment 128 of the BEOL in FIG. 4. A dielectric 116, particularly a low-k dielectric, can be disposed between the first and second comb structures 502, 504, respectively. The comb structures can be fabricated from copper or any other known conductive material. The dielectric 116 can be silicon dioxide or any other known dielectric material.

The first comb structure 502 has a longitudinal conductive portion 508 and a plurality of transverse conductive portions 510, 512, and 514. Likewise, the second comb structure 504 has a longitudinal portion 516 and a plurality of transverse portions 518, 520, and 522. In the configuration of FIG. 5, transverse portion 510 of the first comb structure 502 is oriented substantially parallel to and between transverse portions 518 and 520 of the second comb structure 504. Similarly, transverse portion 512 of the first comb structure 502 is oriented substantially parallel to and between transverse portions 520 and 522 of the second comb structure 504. Transverse portion 514 is aligned substantially parallel to transverse portions 510 and 512 of the first comb structure and transverse portions 518, 520, and 522 of the second comb structures. In other embodiments, the comb structures can have additional or fewer transverse portions. Also, the transverse portions can be disposed at various angles rather than substantially parallel to one another. A metal layer can include more than two comb structures as well.

As described above, the comb structures are fabricated in the second sensor segment 128. In other embodiments, the comb structures can be fabricated in one or more different sensor segments. In addition to the comb structures, a serpentine conductive path 506 can be fabricated such that it winds between the first comb structure 502 and second comb structure 504. The serpentine 506 can be formed from copper or any other conductive material. A sensor that includes a first probe 124 and a second probe 126 can be used to detect delamination of the dielectric material 116. For instance, the first probe 124 can be coupled to a first end 524 of the serpentine 506 and the second probe 126 can be coupled to a second end 526 of the serpentine 506. An electrical signal can pass through the serpentine 506 between the first probe 124 and second probe 126. The sensor can check for signal continuity through the serpentine 506. In FIG. 4, for example, the TSV 104 can expand and contract during thermal cycling and thus create stress on the dielectric material 116. The dielectric material 116 between the first sensor segment 114 and second sensor segment 128 can crack. If the cracking of the dielectric material 116 is severe enough, the serpentine 506 can break and therefore increase the resistance along the serpentine 506 or possibly create an open circuit between the first end 524 and second end 526.

Alternatively, the first probe 124 of the sensor can be coupled to the first comb structure 502 and the second probe 126 can be coupled to the serpentine 506. The sensor can detect a condition referred to as bridging. Bridging can occur when the dielectric material 116 between the first comb structure 502 and serpentine 506 breaks or cracks and thereby reduces insulation between structures. A detectable leakage of current, for example, can be measured by the sensor. Alternatively, the first probe 124 of the sensor can be coupled to the second comb structure 504 and bridging can be detected between the serpentine 506 and the second comb structure 504.

In another embodiment, capacitance can be measured between conductive paths to detect delamination. For instance, in FIG. 5, capacitance could be measured between the first probe 124 and the second probe 126. Any damage to the dielectric material 116 could be detectable because there would be a lack of continuity between probes. In this form, the comb structures and serpentine form at least partially parallel conductive paths and thus act as a parallel plate capacitor. When the dielectric material 116 is damaged, the sensor can detect that the capacitor is "leaky" or there is a signal continuity problem.

A method of forming an interconnect sensor for detecting delamination of a dielectric material due to a mismatch in the coefficient of thermal expansion is also provided. The method includes forming a conductive path between at least two back end of line metal layers. The conductive path can be fabricated as a via or a plurality of vias. In either case, the conductive path can be fabricated from copper or any other conductive material. The at least two back end of line metal layers can be separated by a dielectric material such as silicon dioxide. The dielectric material can be a low-k dielectric. The conductive path can be coupled to a first probe structure and second probe structure. Likewise, the conductive path can be mechanically coupled to a stress inducing structure. Once formed, the sensor can detect delamination of the dielectric material due to a mismatch of coefficients of thermal expansion between the dielectric material and stress inducing structure.

A different method of forming an interconnect sensor to detect delamination due to a mismatch in the coefficient of thermal expansion is provided. The method includes fabricating a first conductive path and a second conductive path at least partially parallel to one another. The first conductive path and second conductive path can be comb structures as described in FIGS. 4 and 5 above. A stress inducing structure such as a TSV or solder ball can be provided such that the first and second conductive paths are mechanically coupled to the stress inducing structure. The method can include fabricating a serpentine conductive path between the first and second conductive paths. The first and second conductive paths can be fabricated in the same back end of line layer.

Figure 6:
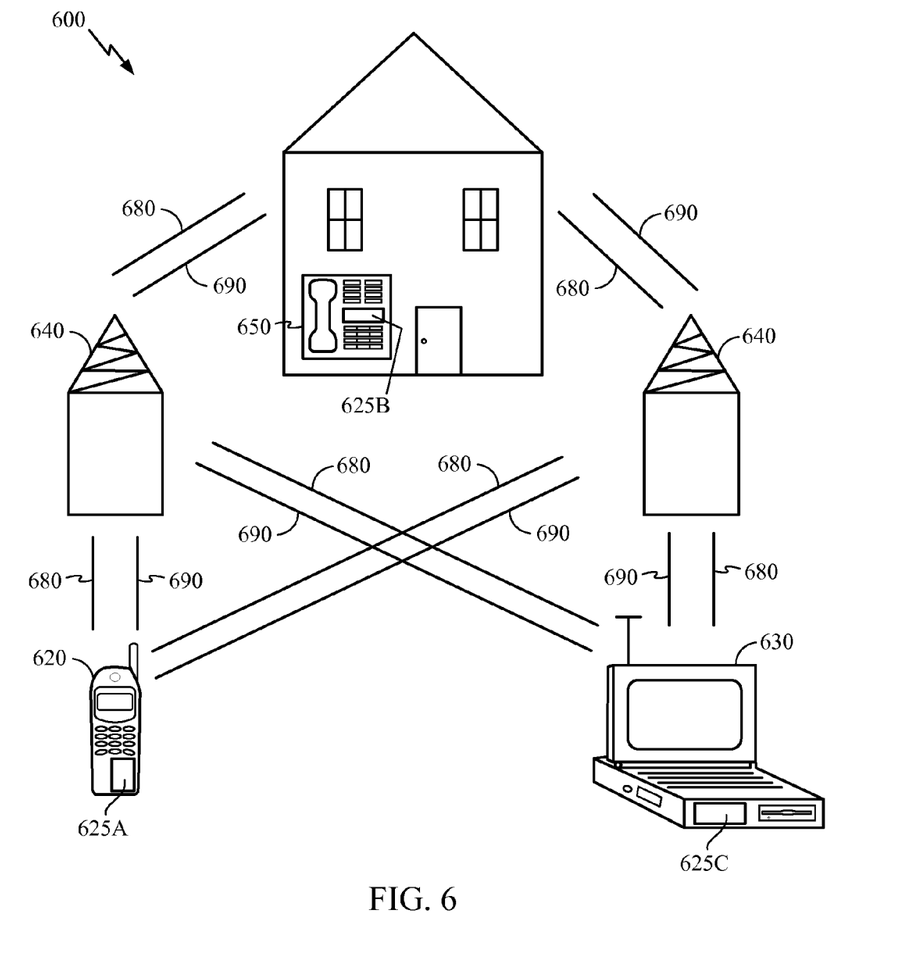
FIG. 6 is a block diagram showing an exemplary wireless communication system in which a package substrate includes an interconnect sensor for detecting delamination.

FIG. 6 shows an exemplary wireless communication system 600 in which an embodiment of an electronic package with an interconnect sensor for detecting delamination of a dielectric material may be advantageously employed. For purposes of illustration, FIG. 6 shows three remote units 620, 630, and 650 and two base stations 640. It should be recognized that typical wireless communication systems may have many more remote units and base stations. Any of remote units 620, 630, and 650, as well as the base stations 640, may include an electronic package with an interconnect sensor for detecting delamination of a dielectric material such as disclosed herein. FIG. 6 shows forward link signals 680 from the base stations 640 and the remote units 620, 630, and 650 and reverse link signals 690 from the remote units 620, 630, and 650 to base stations 640.

In FIG. 6, remote unit 620 is shown as a mobile telephone, remote unit 630 is shown as a portable computer, and remote unit 650 is shown as a fixed location remote unit in a wireless local loop system. For example, the remote units may be cell phones, hand-held personal communication systems (PCS) units, portable data units such as personal data assistants, or fixed location data units such as meter reading equipment. Although FIG. 6 illustrates certain exemplary remote units that may include an electronic package with an interconnect sensor for detecting delamination of a dielectric material as disclosed herein, the package is not limited to these exemplary illustrated units. Embodiments may be suitably employed in any electronic device in which an electronic package with an interconnect sensor for detecting delamination of a dielectric material is desired.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An interconnect sensor for detecting delamination, comprising:
a first probe structure and a second probe structure;
a via layer containing a via and disposed between at least two back end of line metal layers, the via forming a conductive path between the first probe structure and the second probe structure;
wherein, the via is mechanically coupled to a stress inducing structure; and
further wherein, the via is configured to alter the conductive path in response to mechanical stress caused by the stress inducing structure.

2. The interconnect sensor of claim 1, further comprising a plurality of vias.

3. The interconnect sensor of claim 1, further comprising a dielectric, and wherein the dielectric comprises a low k dielectric.

4. The interconnect sensor of claim 3, wherein the stress inducing structure is fabricated using a material with a coefficient of thermal expansion about five times greater than a coefficient of thermal expansion of the dielectric.

5. The interconnect sensor of claim 1, wherein the stress inducing structure comprises a through silicon via.

6. A sensor for detecting delamination, comprising:
a first probe structure and a second probe structure;
a layer containing a first conductive path mechanism and proximate a first back end of line metal layer, the first conductive path mechanism forming a conductive path between the first probe structure and the second probe structure;
wherein, the first conductive path mechanism is mechanically coupled to a through silicon via; and
further wherein, the first conductive path mechanism is configured to alter the conductive path in response to mechanical stress caused by the through silicon via.

7. The sensor of claim 6, further comprising:
a second back end of line metal layer,
wherein the first conductive path mechanism is a via, and
wherein the layer containing the via is disposed between at least the first and second back end of line metal layers.

8. The sensor of claim 7, further comprising a plurality of vias.

9. The sensor of claim 7, further comprising a dielectric, and wherein the dielectric comprises a low k dielectric.

10. The sensor of claim 6, wherein the through silicon via is fabricated using a material with a coefficient of thermal expansion approximately five times greater than a coefficient of thermal expansion of the dielectric.

11. The sensor of claim 6, further comprising:
a second conductive path mechanism, wherein the first and second conductive path mechanisms are at least partially parallel.

12. The method of claim 11, wherein the first and second conductive path mechanisms are mechanically coupled to the through silicon via; and
wherein, the conductivity between the first and second conductive path mechanisms may be altered in response to stress caused by the through silicon via.

13. The sensor of claim 11, wherein the second conductive path mechanism forms a comb structure.

14. The sensor of claim 11, wherein the first and second conductive path mechanisms are disposed in the first back end of line metal layer.

15. The sensor of claim 11, further comprising:
a serpentine conductive path disposed between the first and second conductive path mechanisms.

16. The sensor of claim 6, wherein the first conductive path mechanism forms a comb structure.

17. The sensor of claim 6, wherein the first probe structure comprises a contact to which a first sensor probe can couple.

18. The sensor of claim 6, wherein the second probe structure comprises a contact to which a second sensor probe can couple.

* * * * *